United States Patent [19]

Yon

[11] Patent Number: 4,487,614

[45] Date of Patent: Dec. 11, 1984

[54] ADSORPTION SEPARATION CYCLE

[75] Inventor: Carmen M. Yon, Carmel, N.Y.

[73] Assignee: Union Carbide Corporation, Danbury, Conn.

[21] Appl. No.: 552,337

[22] Filed: Nov. 16, 1983

[51] Int. Cl.³ ............................................. B01D 53/04
[52] U.S. Cl. ............................................. 55/33; 55/59; 55/75; 203/19; 203/41; 568/917
[58] Field of Search ............... 34/32, 36, 37, DIG. 1; 55/30, 31, 33, 59, 75, 88; 202/42; 203/18, 19, 41, 42; 568/916, 917

[56] References Cited

U.S. PATENT DOCUMENTS

| | | | |
|---|---|---|---|
| 2,137,605 | 11/1938 | Derr | 55/33 |
| 3,343,916 | 9/1967 | Cahn et al. | 55/33 X |
| 4,066,423 | 1/1978 | McGill et al. | 55/88 X |
| 4,273,621 | 6/1981 | Fornoff | 55/33 X |
| 4,276,058 | 6/1981 | Dinsmore | 55/88 X |
| 4,331,456 | 5/1982 | Schwartz et al. | 55/88 X |
| 4,351,732 | 9/1982 | Psaras et al. | 55/33 X |
| 4,373,935 | 2/1983 | Ausikaitis et al. | 55/33 |
| 4,407,662 | 10/1983 | Ginder | 55/33 |
| 4,414,003 | 11/1983 | Blaudszun | 55/59 X |
| 4,421,532 | 12/1983 | Sacchetti et al. | 55/59 X |

Primary Examiner—Robert Spitzer
Attorney, Agent, or Firm—Richard G. Miller

[57] ABSTRACT

In a fixed-bed vapor phase adsorption cycle for bulk separations wherein the heat front generated by the exothermic heat of adsorption is maintained in the bed either in or behind the mass transfer zone, and is subsequently utilized in the purge desorption/regeneration of the bed, improved efficiency and enhanced versatility with respect to the degree of product purity is obtained by treating the regeneration purge gas with a portion of the purified product.

11 Claims, 2 Drawing Figures

ADSORPTION SEPARATION CYCLE

The present process relates in general to the bulk separation of mixtures by selective adsorption of at least one principal constituent thereof using crystalline molecular sieve adsorbents. More particularly the process concerns the vapor phase drying of water-organic azeotropes or near-azeotropes, such as water-ethanol mixtures, by size-selective adsorption of the water constituent on an appropriate molecular sieve using a fixed-bed adsorption system, an adsorption-desorption cycle which utilizes the water heat of adsorption of the adsorption stage in the desorption stage, and a purge desorption/regeneration procedure in which the purge gas is partially dehydrated between passes through the adsorption bed by intimate contact with a portion of the purified product.

In general, drying of fluids, either gases or liquids, by the selective adsorption of the water is economically feasible only when the concentration of water in the fluid is small, i.e., present at a level of a few parts per million up to about 2.5 weight percent. When larger concentrations of water must be removed from a normally vapor-phase mixture, then gas-liquid adsorption or refrigeration is ordinarily resorted to. When such relatively large concentrations of water are to be removed from normally liquid mixtures, distillation procedures are most commonly used. This is not because selective adsorption is incapable of producing a sufficiently water-free product, but rather is due to the fact that the adsorbent's capacity for water is finite and only a fraction of the mass of the adsorbent. It is necessary, therefore, in order to avoid the use of unduly large quantities of adsorbent, to use a smaller and reasonable mass of adsorbent and to periodically and frequently regenerate it by desorption of at least some of its water loading in order to suitably treat more of the water-containing feedstock. The greater the water concentration of the feedstock, of course, the more frequent the need for regeneration of a given mass of adsorbent. Moreover, to provide for a more or less continuous output of dried product, multiple adsorbent beds must be used, so that when the adsorbent capacity of one bed is exhausted, a fresh bed is placed on stream and the exhausted bed regenerated.

The major energy requirement for such an adsorption process is the regeneration step, where a regeneration fluid must be heated to provide the energy for the endothermic desorption of water, the energy required to raise the adsorbent temperature, the energy required to heat the carrier fluid in the voids, and the energy required to heat up the portion of the vessel in contact with the adsorbent. Because regenerations must be carried out more frequently for high water concentrations, the inefficiencies of energy consumption of an adsorptive process are thus more pronounced compared to alternative processes. These constraints generally limit the applicability of adsorptive drying process to small concentrations of water or to unique applications where alternatives are not feasible for other reasons.

One such application in which the alternative process lack clear superiority to adsorptive bulk drying, is azeotrope liquid drying. In treating these mixtures, extractive or vacuum distillation techniques, which are far more complex and energy-intensive than simple distillation, are required. Nevertheless such alternative processes are still generally preferred over liquid-phase adsorption drying, especially when, as usually is the case, a continuous type of process operation is required. More particularly, where ordinary economic considerations limit the quantities of adsorbent and the number of adsorbent beds which can be employed, continuous adsorption processes of necessity operate using relatively short adsorption and regeneration cycle times. Product recovery thus becomes critical because one bed void-space volume of feedstock must be removed from each bed during each regeneration stage. Because of its high molar density, a liquid is extemely difficult to move about in the adsorption system within the short cycle times imposed.

Although most of the difficulties inherent in liquid-phase bulk drying adsorption processes can be avoided by operating the cycle in the vapor phase, the high water concentration of the feedstock leads to another phenomenon which until recently has been considered so adverse to the stability and predictability of adsorption separation processes that it had been avoided at all costs by those skilled in the art. This phenomenon is commonly referred to in the art as "crossover", and its intentional occurrence in a process for the bulk separation of water from organic compounds has been described in detail in U.S. Pat. No. 4,373,935, the disclosure of which is incorporated by reference herein.

Crossover concerns the relative positions in an adsorbent bed of a mass transfer front and a heat front. Hereinafter in the specification and in the claims, a position ahead of heat front or a mass transfer front means a position between the front and the egress end of the bed with respect to the direction of movement of the fluid stream through the bed which generates the particular front involved. Similarly a position behind such a front is a position between the front and the ingress end of the bed. In the adsorptive drying of a fluid stream as in the present invention, the heat front is created by the heat of adsorption of water. For zeolite adsorbents, about 1,800 BTU's are liberated for every pound of water adsorbed. The heat is generated in the water mass-transfer front which is the interfacial region in an adsorption column between water-saturated adsorbent and activated (or partially activated) adsorbent. For small water concentrations ($<2.5$ wt.%), the heat generated in the front is carried out and ahead of the front by the carrier fluid which is moving at a much higher velocity than the water adsorption front in the bed. This may cause the product fluid to be slightly warmer than the feed fluid but does not affect the adsorption dynamics within the mass transfer front. For high water concentrations (2.5 to 50 wt.%), the heat front generated can coincide with the mass transfer front or be positioned behind the mass transfer front. In such cases the rate at which heat is generated by the adsorption exotherm is greater than the rate that it is carried out of the mass transfer front by the carrier fluid, i.e., the mass transfer front "crosses over" the heat front. Thereafter, adsorption is being carried out at a higher temperature than the feed temperature and reduces the efficiency of the adsorbent for water removal by both lowering the effective water equilibrium capacity and elongating the mass-transfer front, which can cause early breakthrough of water into the product. For these cases the mass transfer front is unstable and its behavior is highly unpredictable for design purposes.

The simple equation set forth below is useful in determining the approximate location of the heat front relative to the location of the mass transfer front in an adsorption bed:

$$R = \frac{(Xi - Xo)}{(Yi - Yo)} \times \frac{Cp(g)}{Cp(s)}$$

where R is the "cross-over ratio" Xi is the adsorbent loading in equilibrium with the feed concentration of adsorbate behind the mass transfer front in terms of lbs. adsorbate per lbs. adsorbent; Xo is the adsorbent residual loading ahead of the mass transfer front which is the result of a previous regeneration step in terms of lbs. adsorbate per lb. adsorbate; Yi is the inlet (feed) adsorbate concentration in terms of lbs. adsorbate per lb. of carrier fluid; Yo is the adsorbate concentration of the bed effluent in equilibrium with Xo in terms of lbs. adsorbate per lb. carrier fluid; Cp(g) is the heat capacity of the carrier fluid in terms of BTU's per lb. of fluid per degree Fahrenheit; and $Cp_{(s)}$ is the heat capacity of the adsorbent bed solids in terms of BTU's per lb. of solids per degree Fahrenheit.

Thus for a zeolite adsorbent system, for values of "R" greater than 5, the heat front is far ahead of the mass transfer front, and heat will normally leave the adsorbent bed before the leading edge of the mass transfer front leaves the bed. For values of "R" of from about 1 to 5, the heat front is located predominantly within the mass transfer front between the leading edge and the stoichiometric point of the first mass transfer front created in the bed, and for values of 0.5 to 1, the heat front is located predominantly behind the stoichiometric point of the first mass transfer front. The initial (starting) bed temperature and the total pressure of the system also have a slight affect upon the crossover ratio "R".

Operating an adsorption process for which "R"=<5 results in a reduction of dynamic adsorption capacity compared with the capacity predicted from isothermal data. Thus the heat generated both lengthens the mass transfer front and lowers the equilibrium capacity because of higher local operating temperature. The heat generated can be distributed throughout the adsorbent bed as a broad pulse or a narrow spike. The maximum temperature experienced is a function of "R", the adsorption dynamics and the initial adsorbent conditions. This temperature must be kept below some maximum level because of the potential destruction of the adsorbent or chemical reaction of the fluid at these extreme temperatures.

The process of the aforesaid U.S. Pat. No. 4,373,935, of which the process of this invention is an improvement, comprises drying an organic feedstock containing at least 2.5 weight percent water by passing it through a fixed bed of an adsorbent having pores small enough to substantially exclude the organic constituent. The passage of the feedstock is through the bed and the residual water loading on the adsorbent are controlled in a manner that the heat front generated coincides with, or trails behind, the water adsorption mass transfer front. Countercurrent regeneration of the bed is begun prior to breakthrough of either the heat front or the water mass transfer front in order to utilize the heat energy still within the bed in the desorption of water.

Because of the relatively large quantity of molecular sieve adsorbent necessitated by the relatively large quantity of water to be removed from the feedstock, which is preferably an azeotrope or near-azeotrope, a relatively large volume of purge gas must be passed through the adsorbent bed during the desorption/regeneration step following the adsorption-purification step. The total volume of purge gas required can be minimized by employing a closed-loop regeneration cycle. In such a cycle the non-sorbable purge gas is passed through the water-loaded bed in a direction counter-current to the direction of flow in the previous adsorption step. The initial effluent gas stream from the bed contains a high concentration of water vapor, and since the purge gas is at least somewhat above ambient temperature, a substantial portion of this water vapor can be removed by cooling the effluent stream to below its dew point in a knock-out vessel to form liquid water which is readily removed from the system. The remaining gas phase is then heated and again passed through the adsorbent bed being regenerated and the cycle repeated as many times as required.

The closed-loop type of regeneration has also been proposed as an element of one embodiment of the prior known process of U.S. Pat. No. 4,373,935. Inherent in such an embodiment, however, is a limitation on the degree of dehydration, i.e., purity of the organic product. The water content of the product is a function of the temperature and pressure of the adsorption-purification step and of the residual water loading on the molecular sieve adsorbent at the effluent (with respect to the product stream) end of the bed. The lowest water concentration to which the starting water-organic mixture can be dried is that fugacity which is in equilibrium with this residual water loading. The residual water loading is in turn established by the water saturation temperature of the knock-out vessel and by the temperature and pressure of the gas phase from the knock-out vessel which is recycled to the bed. The lowest residual water loading to which the bed can be stripped during regeneration is that loading which is in equilibrium with the water fugacity of the gas phase from the knock-out vessel. Accordingly, since the bed is regenerated counter-current to adsorption in order to prevent breakthrough of the heat front and since the adsorption outlet temperature and pressure are essentially the same as the desorption inlet temperature and pressure by design, the mol fraction of water vapor in the product organic species cannot be less than the mol fraction of water vapor in the regeneration purge gas. It follows, therefore, that the temperature to which the regeneration gas can be cooled determines the lowest water concentration that can be achieved in the product at a given system pressure.

The significance of this fact becomes apparent when it is considered that the most commonly available and least expensive cooling means is the evaporation of water at ambient air conditions, i.e., the well-known tower water cooling system. Such systems can typically only assure that the cooling water produced will be less than 85° F. for 95 percent or more of the total hours during the months of June through September in the temperate zone and assuming normal climatic conditions. Used in an adsorption system as the only means of cooling the water knock-out for recycled regeneration purge gas, the process can barely produce 198 proof ethanol when the system pressure is 5 psig, but can do so more readily at higher pressures. A 199 proof ethanol product requires an operating pressure of at least 25 psig, but an anhydrous grade commercial ethanol product (containing not more than 0.1 wt. % water) cannot be made in a tower water-cooled system at any reasonable operating pressure. Even if the tower water is further chilled using refrigeration apparatus, a reasonable lower temperature limit is about 40° F. in view of the need to avoid freezing of the condensing water. At 40° F., anhydrous grade ethanol can be produced, but only if the system pressure is greater than 35 psig. Of course a chilled-water system is much more costly and energy consumptive than cooling tower systems.

It has now been discovered that the limitations on organic product purity in processes such as hereinbefore described can be largely avoided by the improvement whereby the water content of recycled purge regeneration gas is further dried after passage through a water knock-out by intimately contacting same with a portion of the product organic material. In this manner the recycled regeneration gas is rendered significantly drier by loss of the water absorbed by the product organic material. The drier regeneration gas in turn lowers the residual water loading on the effluent end of the bed during adsorption and hence results in the production of a much drier product. In the drawings:

Figure 1:
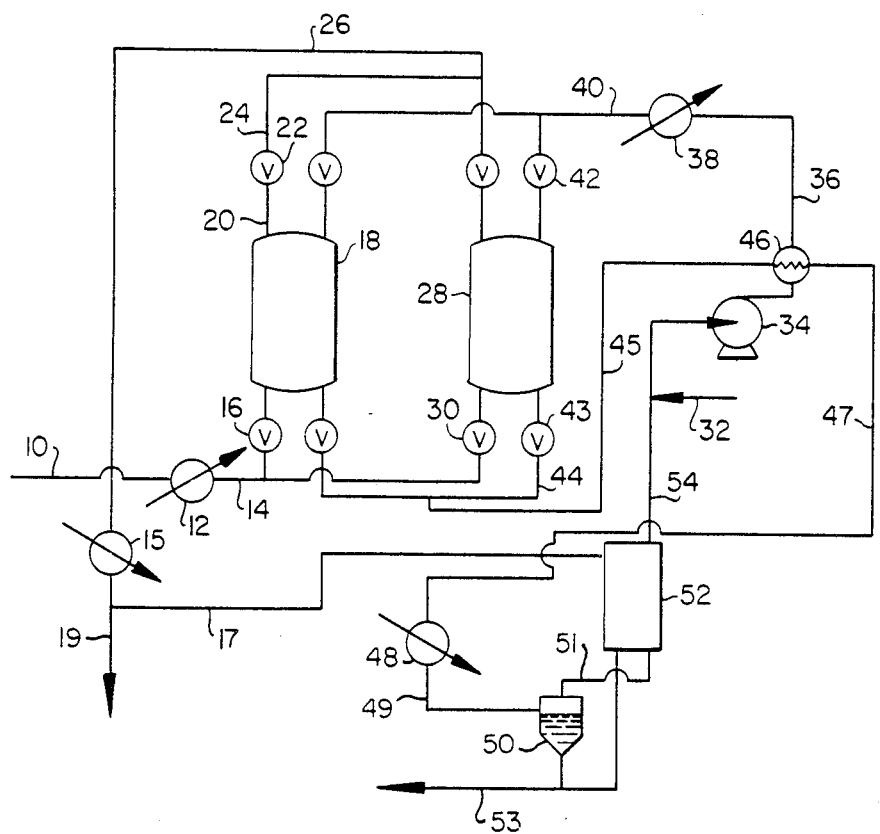
FIG. 1 is a schematic flow diagram of one embodiment of the present invention.

The present improved process can be described as follows:

In an adsorption separation process which comprises:

(a) passing in the vapor phase a feedstock comprising at least 2.5 weight percent water in admixture with at least one organic molecular species into a fixed adsorption bed at a temperature and pressure which prevents the capillary condensation of said organic molecular species, said fixed adsorption bed containing an adsorbent mass consisting essentially of a crystalline zeolitic molecular sieve adsorbent having pores small enough to substantially exclude the said organic molecular species, moving the water adsorption mass transfer front and the coinciding or trailing heat front created in said fixed bed along said bed toward the effluent end thereof to a predetermined point short of breakthrough of either of said front, at least that portion of said molecular sieve adsorbent contacted by said water mass transfer front containing adsorbed thereon, prior to and at the time of contact of said front, at least about 2, and preferably at least about 5, weight percent water, said molecular sieve adsorbent having a capacity for the adsorption of water under the imposed operating conditions greater than the water loading thereon at the time of contact by the water mass-transfer front; (b) from the effluent end of said bed, recovering a product stream containing a lower concentration of water than the feedstock;

(c) terminating the flow of feedstock into said bed prior to breakthrough of either of the heat front and the water mass transfer front, and prior to substantial loss of the heat energy from the bed, commencing the counter-current passage through said bed of an essentially non-sorbable purge gas at a temperature within about 25° F. of the temperature of, and substantially at the same pressure as, the feedstock entering the bed during adsorption step (a), said temperature and pressure being sufficient to prevent capillary condensation of the said organic molecular species of said feedstock, whereby the energy of said heat front is utilized in desorbing water from the adsorbent mass;

(d) continuing the counter-current purging of said bed until the water loading on said adsorbate is essentially the same as at the beginning of adsorption step (a); and (e) repeating adsorption step (a), the improvement which comprises carrying out the counter-current passage of non-sorbable purge gas through the bed in steps (c) and (d) by recycling the said purge gas effluent from said bed through cooling means to lower its temperature below the water dew point thereof whereby liquid water is formed, and intimately contacting the effluent purge gas phase from said cooling means with a liquid phase portion of the product recovered in step (b) to further reduce the water content of said purge gas, separating at least a portion of the said water-enriched liquid phase product from the purge gas and passing the resulting purge gas through the bed.

As used herein the terms mass transfer front, heat front and breakthrough are all intended to have the meaning conventional in the adsorption-separation art. The mass transfer front is the fluid concentration or adsorbent loading profile of the adsorbable component over the mass transfer zone. The adsorbate loading through the transfer zone is essentially a linear function of the fluid phase concentration of the adsorbable component. Similarly the heat front is the temperature profile of the adsorbent generated by the heat of adsorption of the adsorbable component—in the present case, water. Breakthrough is said to occur when the leading edge of the mass transfer front or the heat front reaches the effluent end of the bed. Breakthrough is, however, arbitrarily defined, and can be taken as either the minimum detectable concentration or temperature increase in the effluent product or as the maximum allowable increase in these parameters. In the present process, the latter criterion is applied.

The particular species of crystalline molecular sieve employed is not a narrowly critical factor. In all events, however, it should be capable of adsorbing more than 2, preferably more than 5, weight percent water under the process conditions of temperature and pressure, and to substantially exclude from adsorption essentially all of the other constituents of the feedstock under those conditions. Preferably a zeolitic molecular sieve is employed. As will be readily understood by those skilled in the art, the significant adsorption of such materials other than water can be disruptive of the process by, for example, the creation of secondary mass transfer and heat fronts or by partially decomposing on the zeolite and diminishing its adsorptive capacity through coke formation. Thus a zeolite having an effective pore diameter of about 3 Angstroms, such as the potassium cation form of the type A zeolite, is suitable for all feedstocks within the present process, but where the organic constituent is a relatively large molecule, such as benzene, any of the so-called small pore zeolites such as the various cationic forms of zeolite A, zeolite F, zeolite D, zeolite W, zeolite alpha, zeolite phi, mordenite, erionite, clinoptilolite and chabazite can be suitably employed. A comprehensive listing of both synthetic and naturally occurring zeolites is set forth in "Zeolite Molecular Sieves", by D. W. Breck, John Wiley & Sons, New York, NY (1974). A zeolite species of universal applicability in treating the feedstocks of the present process is the potassium-exchanged form of zeolite A in which the pores are about 3 Angstroms in diameter. The type A zeolite structure, moreover, has a very large capacity for the adsorption of water. For most feedstocks, including those in which the organic constituent is ethanol or a higher alcohol, small pore mordenite, particularly the mineral form, such as is commercially available under the Union Carbide Corporation designation AW-300, is also highly effective and is a preferred adsorbent.

The feedstocks suitably treated are any mixtures of water with one or more organic compounds which contain at least 2.5 weight percent water. Preferred feedstocks are those which cannot be dried by conventional distillation techniques, i.e., are either aqueous azeotropes or can form azeotropic mixtures by appropriate changes in the relative proportions of their constituents. Such mixtures include those wherein the organic constituent is one or a mixture of two or more of ethanol, isopropanol, sec-butanol, tert-butanol, alkyl alcohol, benzene, tetrahydrofuran, dioxane, toluene, diethyl ether, di-iso-propyl ether, ethylene chloride, n-propyl formate, methyl acetate, ethyl acetate, methyl propionate, ethyl-iso-butyrate, n-propyl nitrate, methyl ethyl ketone, formic acid, methyl formate and pyridine. Particularly preferred feedstocks are mixtures of one or more primary alcohols having from 2 to 5 carbon atoms inclusive with water in which the water content is from 2.5 to about 20 weight percent. Above about 20 weight percent water the adsorption-desorption cycle times become undesirably short and heat rise peaks in the bed are also higher than preferred. An especially preferred feedstock is an ethanol-water mixture containing from about 3.5 to 11.9 volume-% (4.4 to 14.3 weight-%) water.

The temperature and pressure conditions for the adsorption step must be selected to maintain the feedstock in the vapor phase and prevent capillary condensation of the organic constituent in the adsorbent. It is preferred that the feedstock temperature be within the range of about 200° F. to 450° F. and at appropriate corresponding pressure within the range of about 1 atmosphere (absolute) up to about 100 psia. At higher pressures it is possible for the density of the feedstock to be sufficiently high to force the heat front ahead of the water mass-transfer front. During the counter-current purge-desorption step the temperature of the non-sorbable purge gas entering the bed can be from about 200° to 475° F., and is preferably within 25° F. of the temperature of the feedstock stream during adsorption. The adsorption-desorption cycle is preferably isobaric or nearly isobaric.

The purge gas utilized in the desorption/regeneration stages of the process can be any vapor phase compound which is not harmful to the zeolite absorbent, does not appreciably react with the feedstock constituents under the imposed conditions and which is not appreciably adsorbed by the zeolite. The non-adsorbability of the purge gas can be due either to molecular size exclusion or to a weak adsorptive attraction between it and zeolite. Thus purified product from a previous adsorption step can be used or, and preferably, a normally gaseous extraneous medium such as nitrogen, hydrogen, helium, carbon dioxide or methane.

In carrying out the purge-desorption steps it is important that at least that portion of the regenerated bed which is contacted with the water mass transfer front during the subsequent adsorption step, contains at least about 2, and preferably at least about 5 weight percent water. Accordingly, it is not essential that the entire bed have a level loading of water, and in fact as a practical matter it will not. Since the water loading on the egress end of the bed during adsorption determines the concentration of water in the product, it can be advantageous to carry out the counter-current purge-desorption in such a manner as to minimize the water loading beyond the point along the bed length reached by the water mass transfer front, while assuring that the adsorbent actually passed over by that mass transfer front contains the requisite amount of water loading to prevent unduly high thermal peaks.

The process is illustrated by the following specific embodiment described with reference to FIG. 1 of the drawings.

EXAMPLE 1

Figure 2:
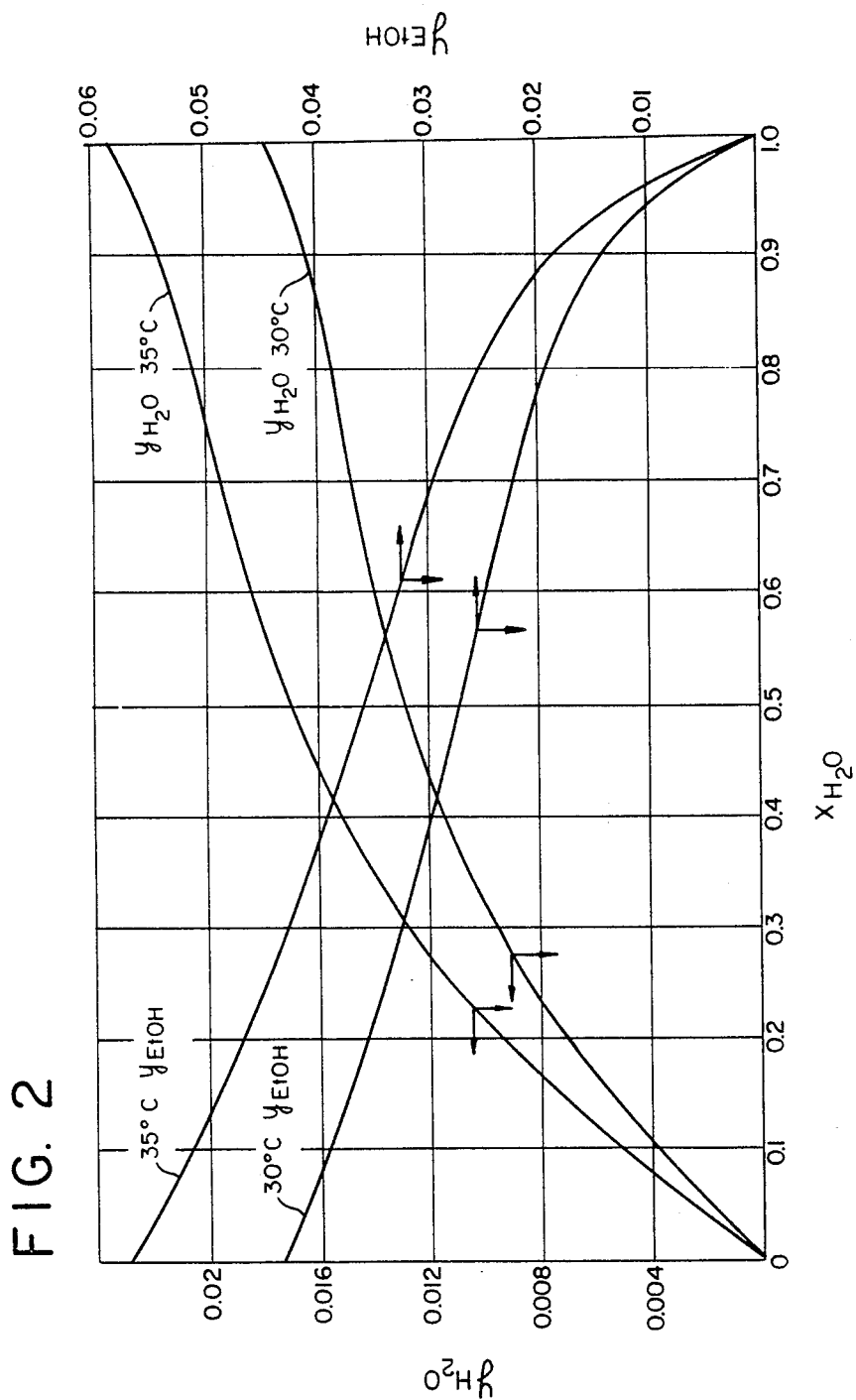
FIG. 2 is a plot showing liquid/vapor equilibrium data for the system ethanol/water/nitrogen at 85° F. and 95° F. and a pressure of 35 psig.

With reference to the adsorption system shown in FIG. 1, the adsorption beds 18 and 28 are each packed with 6580 pounds of ⅛" pellets of Type 3A zeolite, which under the process conditions utilized herein, are capable of dehydrating 5 million gallons per year (4100 pounds/hour) of 190 proof ethanol (7.58 weight percent water) feedstock to an anhydrous grade (<1000 ppm water, weight basis) ethanol. Feedstocks 190 proof ethanol is fed into the system at the rate of 99.4 pound moles per hour through line 10 and heater 12 where the temperature is raised to 300° F., and thereafter through line 14, valve 16 and thence into bed 18. As a result of the most recent purge regeneration, the adsorbent in bed 18 contains a residual water loading of 11.5 weight percent. The pressure throughout the system is approximately 40 psia. In bed 18 the water of the feedstock is adsorbed and forms a mass transfer front which moves upward therethrough. The water loading behind the mass transfer front is about 17 weight percent, and as a consequence a significant heat rise of approximately 100° F. occurs resulting in the formation of a heat front which slightly trails the water mass transfer front. The adsorption step in bed 18 is continued for about 15 minutes during which period an anhydrous grade ethanol product (82.2 pound mols/hr ethanol and 0.21 pound mol/hr water) is obtained as the bed effluent. The ethanol product passes through line 20, valve 22, line 24, line 26, and water cooler 15 wherein it is condensed to the liquid phase at a temperature of 95° F. The major proportion (60%) of the liquid ethanol product is removed from the system through line 19, and the remaining proportion (32.9 pound mols/hr ethanol and 0.08 pound mol/hr water) is diverted through line 17 and utilized in drying the purge regeneration gas stream as described hereinafter. At the end of the 15-minute adsorption step, during which period neither the water mass transfer front nor the heat front have broken through the bed 18, the feedstock is diverted to bed 28 through line 14 and valve 30. Bed 18 is thereupon regenerated in the same manner as bed 28 was during the previous 15-minute period. At the beginning of the regeneration step with respect to bed 28, the bed was in the same condition as bed 18 is at this point. The regeneration is accomplished using nitrogen as a purge gas introduced into the system through line 32. Line 32 also serves as the means to introduce make-up purge gas into the operating system as required. The purge gas is forced at a rate of 658 pound mols/hr. and at a pressure of 40 psia by blower 34 through heat exchanger 46, line 36, heater 38 where its temperature is raised to 300° F., line 40, valve 42 into bed 28 in a flow direction counter-current to the direction of flow of the feedstock stream thereinto. The initial action of the nitrogen purge gas stream is to flush the void space of the bed and thereafter to partially desorb the water from the zeolite adsorbent. Purge gas and desorbed water leave the bed 28 through valve 43, line 44, line 45, heat exchanger 46, line 47 and are passed through cooler 48 wherein the temperature is lowered to 95° F. and then passed through line 49 to knock-out pot 50 wherein 11.6 pound mols/hr ethanol and 8.07 pound mols/hr water are condensed and recovered through line 53 as a recycle feed in combination with the effluent from absorber 52, infra. This recycle feed comprises 32.9 pound mols/hr. ethanol and 17.07 pound mols/hr. water. The effluent gas phase from knock-out pot 50 comprises 658 pound mols/hr nitrogen, 26.6 pound mols/hr ethanol and 10.66 pound mols/hr water and is passed through line 51 to the bottom of absorber 52. The preferred type of absorber, and the one employed herein, is a trayed column, but other equipment such as spray columns, wetted wall columns, thin-film contactors and packed towers are satisfactory for specific applications. The 40 percent portion of dried ethanol product which was diverted through line 17 is at a temperature of about 95° F. and is passed to the top of absorber 52. The flow rate of the liquid ethanol downward through the absorber is 1.25 times the minimum amount required to dry the purge gas passing upward through the absorber in contact with the dry ethanol to the desired level. The spent liquid leaves the column bottom enriched in water. The trayed absorber column, 52, was designed using the vapor/liquid equilibrium data of FIG. 2 of the drawings. The vapor and liquid leaving each theoretical tray are taken to be in equilibrium. The absorber is assumed to be isothermal. The liquid ethanol flow rate is 1.25 times the minimum required to accomplish the separation. The column, then, requires 6 and a partial theoretical stages. The tower would have a 3-foot ID with 15-inch minimum tray spacing. The resulting tray-by-tray compositions are set forth in Table 1 below.

| TRAY* | L(LB MOL/HR) | $X_{H_2O}$ | G(LB MOL/HR) | $Y_{EtOH}$ | $Y_{H_2O}$ |
|---|---|---|---|---|---|
| FEED | 32.98 | 0.00255 | — | — | — |
| 1 | 32.92 | 0.04530 | 697.94 | 0.05470 | 0.00255 |
| 2 | 32.80 | 0.08460 | 697.88 | 0.05260 | 0.00457 |
| 3 | 32.60 | 0.12377 | 697.76 | 0.05060 | 0.00664 |
| 4 | 32.31 | 0.16622 | 697.56 | 0.04852 | 0.00822 |
| 5 | 31.79 | 0.21663 | 697.27 | 0.04619 | 0.01013 |
| 6 | 30.79 | 0.28365 | 696.75 | 0.04330 | 0.01232 |
| 7** | 30.30 | 0.29970 | 695.75 | 0.03930 | 0.01497 |
| FEED | — | — | 695.26 | 0.03828 | 0.01557 |

*Numbering from top
**A partial equilibrium stage

When, as is the present case, the feedstock to the process is the product of a separation process such as distillation where major water removal is accomplished to achieve near azeotropic composition, the liquids from the knock-out vessel 50 and the absorber 52 can be combined and recycled to the appropriate point for water rejection. (For example, in a fermentation plant the combined stream can be pumped to the "beer" well or introduced as liquid onto the "beer" still tray which most nearly approximates the water concentration. For other applications, the knock-out pot liquid, or the overflow of liquid from the absorber bottom tray, whichever is richer in water, may be the means of rejecting water from the system. The stream which is leaner in water is recycled to adsorber 18 for further water removal.) The dried regeneration gas flowing from the top of absorber 52 comprises 658 pound mols/hr nitrogen, 38.2 pound mols/hr ethanol and 1.74 pound mols/hr water and is passed through line 54 to blower 34, thus completing the cycle. (The blower can be used at any point in the closed-loop recycle. However, the preferred placement is as shown, so that the heat of compression can reduce the amount of heat added to achieve the adsorber 28 influent temperature.) Because the purge gas is much drier (about one order of magnitude) as a result of the treatment in absorber 52 than would be the case if it were treated in knock-out pot 50, it produces a substantially lower residual water loading on the molecular sieve when the gas regenerates adsorber 28.

In addition to the improvement in drying capability, the present process provides another significant advantage over prior known processes. It is to be noted that after the regeneration step is complete in adsorber 28, there remains isolated in the head space, inter-particle voids and macropore voids of the bed a considerable amount of nitrogen. For beds of the size employed in the foregoing example, this amount of nitrogen would be, conservatively, about 100 cu. ft. Since one bed is regenerated every 15 minutes, at least 400 cu ft/hr of nitrogen would be lost if it were merely flushed from the bed during the next adsorption-separation stroke. If, moreover, this nitrogen stream is vented to the atmosphere, it could create an air pollution problem because of its ethanol content. There is also the disadvantage of losing the valuable ethanol.

A similar situation exists after the completion of the adsorption step in bed 18, only in this instance the bed void space is filled with feedstock which is rich in ethanol and is readily condensable. When this bed-volume of ethanol reaches cooler 48 during the regeneration of the bed, it is almost totally condensed and removed in knock-out pot 50. Because the bed regeneration is carried out in a "closed loop" mode, this condensation of a large volume of vapor will cause a rapid decrease in pressure. In a conventional process, this decrease would be compensated for by the introduction of make-up nitrogen through line 32.

In the present process, however, the non-condensible purge gas which is forced from the adsorption bed in admixture with product ethanol during the adsorption stroke can readily be diverted from the product ethanol stream along with that portion of product ethanol which is used to dry the regeneration gas stream in absorber 52 and be recycled along with the bulk of the regeneration gas as hereinabove described. This avoids the undue waste of purge nitrogen, product alcohol and the attendant air pollution problem of prior known processes with only minimal addition of process equipment such as pressure valves, purge tanks and the like.

The ethanol-water mixture which is in the bed void space behind the water mass transfer zone at the end of an adsorption step, can also be recovered. At the beginning of the countercurrent regeneration step, for example in bed 28, the first portion of nitrogen entering the bed through valve 42 serves to purge the ethanol and water out through valve 30 and line 14, and can then be directed through valve 16 along with feedstock entering the system through line 10. After the bulk of the ethanol-water mixture has been forced from bed 28, the effluent nitrogen purge stream is then directed through valve 43 and the recycle purge begun as described hereinabove.

What is claimed is:
1. In an adsorption separation process which comprises:
(a) passing in the vapor phase a feedstock comprising at least 2.5 weight percent water in admixture with at least one organic molecular species into a fixed adsorption bed at a temperature and pressure which prevents the capillary condensation of said organic molecular species, said fixed adsorption bed containing an adsorbent mass consisting essentially of a crystalline zeolitic molecular sieve adsorbent having pores small enough to substantially exclude the said organic molecular species, moving the water adsorption mass transfer front and the coinciding or trailing heat front created in said fixed bed along said bed toward the effluent end thereof to a predetermined point short of breakthrough of either of said front, at least that portion of said molecular sieve adsorbent contacted by said water mass transfer front containing adsorbed thereon prior to and at the time of contact of said front, at least about 2, and preferably at least about 5, weight percent water, said molecular sieve adsorbent having a capacity for the adsorption of water under the imposed operating conditions greater than the water loading thereon at the time of contact by the water mass-transfer front;

(b) from the effluent end of said bed, recovering a product stream containing a lower concentration of water than the feedstock;

(c) terminating the flow of feedstock into said bed prior to breakthrough of either of the heat front and the water mass transfer front, and prior to substantial loss of the heat energy from the bed, commencing the counter-current passage through said bed of an essentially non-sorbable purge gas at a temperature within about 25° F. of the temperature of, and substantially at the same pressure as, the feedstock entering the bed during adsorption step (a), said temperature and pressure being sufficient to prevent capillary condensation of the said organic molecular species of said feedstock, whereby the energy of the said heat front is utilized in desorbing water from the adsorbent mass;

(d) continuing the counter-current purging of said bed until the water loading on said adsorbate is essentially the same as at the beginning of adsorption step (a); and (e) repeating adsorption step (a), the improvement which comprises carrying out the counter-current passage of non-sorbable purge gas through the bed in steps (c) and (d) by recycling the said purge gas effluent from said bed through cooling means to lower its temperature below the water dew point thereof whereby liquid water is formed, and intimately contacting the effluent purge gas phase from said cooling means with a liquid phase portion of the product recovered in step (b) to further reduce the water content of said purge gas, separating at least a portion of the said water-enriched liquid phase product from the purge gas and passing the resulting purge gas through the bed.

2. Process according to claim 1 wherein the feedstock is a mixture of water and an organic molecular species which can form an azeotrope.

3. Process according to claim 1 wherein the feedstock is an azeotrope.

4. Process according to claim 1 wherein the organic molecular species is a primary alcohol containing from 2 to 5 carbon atoms inclusive.

5. Process according to claim 2 wherein the organic molecular species is a member selected from the group consisting of ethanol and isopropanol.

6. Process according to claim 3 wherein the organic species is a member selected from the group consisting of ethanol and isopropanol.

7. Process according to claim 4 wherein the temperature of the feedstock entering the adsorption bed is within the range of 200° F. to 450° F. and the pressure is within the range of about 1 to about 6.8 atmospheres.

8. Process according to claim 7 wherein the zeolitic molecular sieve adsorbent is a zeolite having the mordenite crystal structure.

9. Process according to claim 7 wherein the zeolitic molecular sieve adsorbent is a Type A zeolite having pore diameters of about 3 Angstroms.

10. Process according to claim 7 wherein at least that portion of the molecular sieve adsorbent in the adsorption bed which is contacted by the water mass transfer front during step (a) contains, prior to and at the time of contact of said front, at least 2 weight percent water.

11. Process according to claim 10 wherein the feedstock is a mixture consisting essentially of water and ethanol wherein the water content is from 5 to 12 volume percent of the overall mixture.

* * * * *